United States Patent [19]

Dotta

[11] Patent Number: 4,991,378

[45] Date of Patent: Feb. 12, 1991

[54] MACHINE FOR MANUFACTURING AND PACKAGING ADHESIVE PLASTERS

[76] Inventor: Giorgio Dotta, Via Alamandini 10 - 40136, Bologna, Italy

[21] Appl. No.: 280,789

[22] Filed: Dec. 7, 1988

[30] Foreign Application Priority Data

Dec. 16, 1987 [IT] Italy .................................. 3733 A/87

[51] Int. Cl.⁵ .......................................... B65B 9/02
[52] U.S. Cl. .................................... 53/520; 53/553; 156/252; 156/269; 156/519; 156/522; 156/552
[58] Field of Search ................. 53/154, 155, 157, 450, 53/520, 548, 553, 555; 83/255, 553, 562, 695; 156/252, 269, 517, 519, 522, 552, 580, 583.5

[56] References Cited

U.S. PATENT DOCUMENTS 2,563,071 8/1951 Salfisberg ........................... 53/553 X
2,680,943 6/1954 Petersen ............................. 53/520 X
2,862,846 12/1958 Blackford et al. ............... 156/269 X

*Primary Examiner*—Robert L. Spruill
*Assistant Examiner*—Linda B. Johnson
*Attorney, Agent, or Firm*—Guido Modiano; Albert Josif

[57] ABSTRACT

The machine includes, arranged in a line, a roller advancement device for intermittently advancing a band of supporting material having an adhesive face, a perforation station bearing a punch for providing a series of evenly spaced perforations on the band of supporting material, an auxiliary band being attached to the band of supporting material to increase the band of supporting material's resistance to deformation, a station with rollers and a linearly actuated blade for feeding and cutting a band of bandage material into segments, a roller advancement device for spacing and coupling the bandage segments onto the adhesive face of the supporting material, a roller advancement device for superimposing band-like protective films onto the adhesive face of the supporting material having the bandage segments attached thereon, thereby forming a composite band, a die-cutting station bearing a cutting element for transversely cutting the composite band in an intermediate position between the bandage segments so as to define individual adhesive plasters, a roller device for the spaced insertion of the adhesive plasters between a pair of bands of packaging paper, thereby forming a final product band, a cutting station with a roller device and a linearly actuated cutting blade for cutting the resulting final product band or for providing incisions thereon.

36 Claims, 2 Drawing Sheets

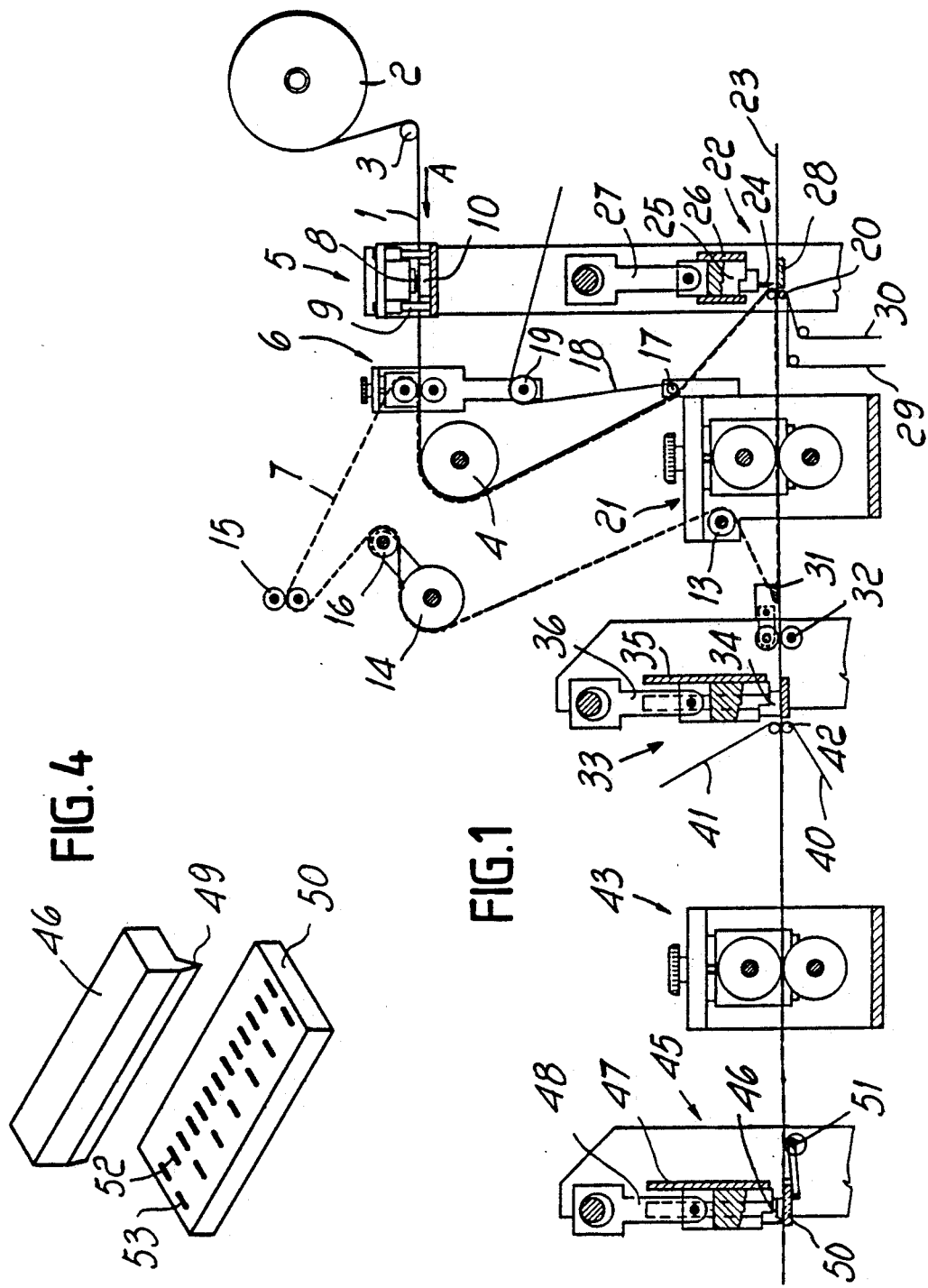

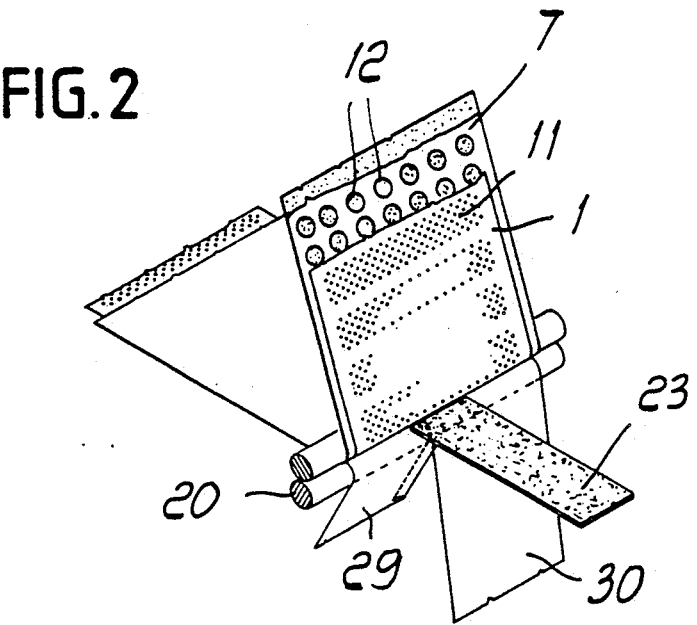
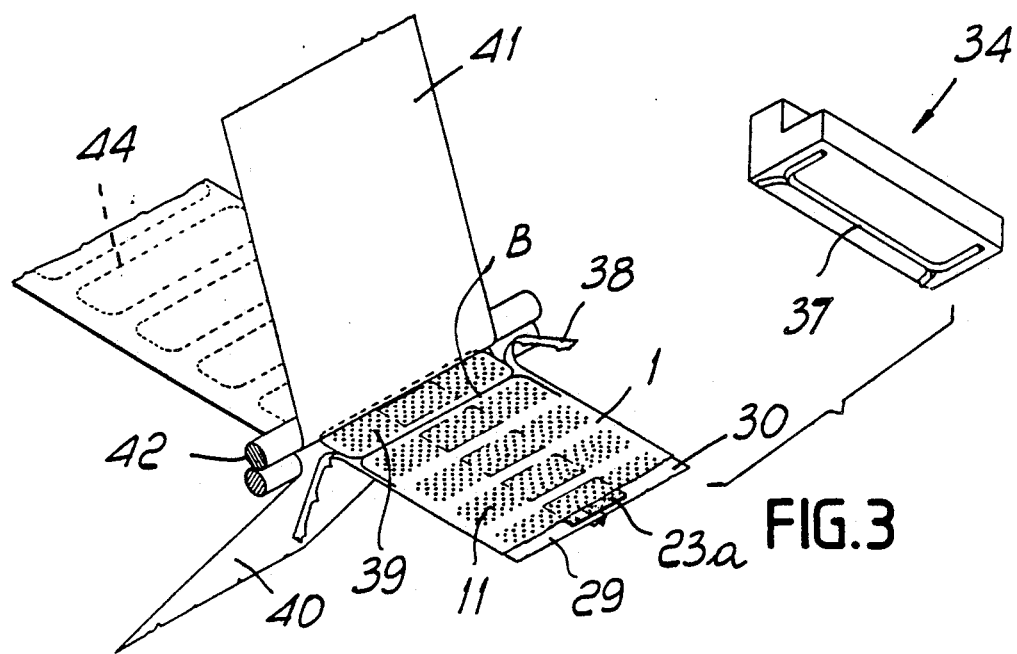

1

MACHINE FOR MANUFACTURING AND PACKAGING ADHESIVE PLASTERS

BACKGROUND OF THE INVENTION

The present invention relates to a machine for manufacturing and packaging adhesive plasters.

As is known, machines are used to manufacture medicated adhesive plasters; such machines compose a band of gauze with a band of supporting material having an adhesive face, cut the individual adhesive plasters from the composite band and package said adhesive plasters in paper packages. These machines sometimes operate intermittently and the advancement of the composite band must be halted to perform some of the steps of the cycle. Such machines have, however, various functional disadvantages, in particular as an effect of the arrangement of the elements which compose them. Continuously operating machines have also been proposed which are capable of achieving a higher production speed and therefore greater productivity. A consequence of this operating speed, however, is the fact that continuous machines are scarcely precise and therefore provide a product of poor quality. The need for frequent maintenance is also often observed.

SUMMARY OF THE INVENTION

The aim of the present invention is to solve the above described problem by providing a machine which automatically manufactures and packages high quality adhesive plasters in an easily controllable and adjustable manner, without functional disadvantages.

Within the scope of this aim, a further object of the present invention is to provide a machine which is simple in concept and reliable in operation, has limited dimensions and is versatile in use according to the different types of adhesive plaster to be manufactured and packaged.

This aim and this object are both achieved, according to the invention, by a machine for manufacturing and packaging adhesive plasters, characterized in that it comprises, means for intermittently advancing a band of supporting material having an adhesive face, a station for feeding and cutting a band of bandage material into segments, means for coupling said bandage segments to said adhesive face of said supporting material, means for superimposing band-like protective films on said adhesive face of the supporting material comprising said bandage segments, a die-cutting station bearing means for transversely cutting the band composed of said supporting material, of said bandage segments and of said protective films in an intermediate position between said bandage segments so as to define individual adhesive plasters, means for the spaced insertion of said adhesive plasters between a pair of bands of packaging paper.

BRIEF DESCRIPTION OF THE DRAWINGS

Further characteristics and advantages of the invention will become apparent from the detailed description of a preferred embodiment of a machine for manufacturing and packaging adhesive plasters, illustrated only by way of non-limitative example in the accompanying drawings, wherein:

FIG. 1 is a schematic lateral and partially sectional view of the machine according to the invention;

FIG. 2 is a partial isometric view of the means for coupling the bandage band to the supporting material;

FIG. 3 is a partial exploded isometric view of the die-cutting station;

FIG. 4 is an isometric view of said means for cutting the band or providing incisions thereon.

DESCRIPTION OF THE PREFERRED EMBODIMENTS

With particular reference to the above described figures, the machine according to the invention substantially defines a line along which successive advancement means advance stepwise a band 1 of supporting material unwinding from a reel 2 having a horizontal axis. In a known manner, the supporting material 1 has an adhesive face on which a band of siliconized paper having a protective function is initially applied.

After the reel 2, in the unwinding direction A, the supporting material unwinds horizontally between a pair of rollers 3 and 4, between which a perforation station 5 and a roller advancement device 6 are arranged. An auxiliary band 7 is adapted to be superimposed on the supporting material 1 at the roller device 6; said auxiliary band increases said supporting material's resistance to deformation in relation to the perforations provided thereon.

The station 5 has a sort of punch 8 actuated reciprocatingly on vertical sliding columns 9 so as to co-operate with an opposite fixed die 10. The punch 8 provides a series of perforations 11 on the band 1 at appropriately adjustable distances, as shown in FIGS. 2 and 3; these perforations are intended to improve the transpiration of the adhesive plaster. The auxiliary band 7 is in turn constituted by a layer of supporting material having an adhesive face on which a band of paper bearing perforations 12 is applied. The auxiliary band 7 adheres to the supporting material 1 through the perforations 12, on the face opposite to the face of said supporting material to which the band of siliconized paper is applied. The auxiliary band 7 is closed on itself in a loop, and in the region where it does not adhere to the supporting material 1 it winds on a series of return rollers 13, 14 and 15 and on a tensioning roller 16.

The supporting material 1 separates from the band of siliconized paper 18 after the roller device 6, at a roller 17; the band of siliconized paper then winds onto a roller 19.

The supporting material 1 then engages a pair of opposite rollers 20 after which it advances on a horizontal plane by a roller device 21. A station 22 for feeding and cutting a gauze, or bandage, band 23 is arranged in a position immediately adjacent to said rollers 20; said gauze band is fed horizontally on the unwinding plane of said supporting material by means not illustrated in the figures.

The station 22 has a blade 24 supported by a body 25 vertically guided along a guide 26 and actuated reciprocatingly by means of an eccentric-connecting rod assembly 27; the blade acts in contrast with an appropriately sprung abutment 28. The cutting station 22 is controlled so as to cut segments 23a of the gauze band 23 which, as shown in FIG. 2, are retained on the adhesive surface of the band of supporting material 1 and are regularly spaced, each at the central region of a series of perforations 11.

A pair of protective films 29 and 30 are furthermore immediately superimposed on the supporting material 1 on said adhesive face between the rollers 20, thereby forming a composite band; said films cover said face on opposite sides and partially overlap at the centerline of the band (see FIG. 2).

The auxiliary band 7 separates from the composite band after the roller advancement device 21 by means of a return element 31. The composite band is then sent, by means of a further pair of rollers 32, to a die-cutting station 33. Said station 33 comprises a cutting element 34 vertically slidably guided on a guide 35 and reciprocatingly actuated by means of an eccentric-connecting rod assembly 36. The cutting element 34 has a substantially H-shaped blade 37 adapted, as can be clearly seen from FIG. 3, to produce a cutting line B transversely to the composite band in an intermediate position between one series of perforations 11 and the next, and to shape the ends of the adhesive plasters by removing related scrap portions 38.

Individual adhesive plasters 39 are thus completed at each stroke of the cutting element 34 and are fed between a pair of packaging papers 40 and 41 which unwind on the same horizontal plane between a pair of rollers 42 arranged immediately adjacent to the station 33. The packaging papers 40 and 41 are caused to advance by a roller device 43 arranged after the rollers 42. It should be noted that the advancement speed of the packaging papers 40 and 41 with respect to the feed speed of the adhesive plasters 39 is such that the latter are appropriately spaced in the package, as indicated by the broken lines 44. The packaging papers with the individual adhesive bandages therebetween form a final product band.

After the roller device 43 there is a cutting element 45 constituted by a cutter 46 vertically slidably guided on a guide 47 and actuated reciprocatingly by means of an eccentric-connecting rod assembly 48. The cutter 46 has a blade 49 which, as shown in detail in FIG. 4, co-operates with an abutment 50 underlying the composite band. The abutment 50 is movable on the advancement plane of the band upon the actuation of a crank 51 so as to alternately arrange a smooth surface, a surface bearing a series of closely spaced cuts 52 or a surface bearing a series of widely spaced cuts 53 opposite the blade 49. It is thus possible to cut the individual adhesive plasters or to provide a series of closely or widely spaced incisions which respectively define a cutting line or a folding line of the composite band.

The operation of the machine is easily understandable from the above description. It is apparent that the invention achieves the intended aims. In particular the problem of having poor access due to the arrangement of the various elements, arising in known intermittent machines, is solved. The machine according to the invention in fact has the motorization elements on one side and is free and easily accessible on the other.

In the practical embodiment of the invention, the materials employed as well as the shapes and dimensions may be any according to the requirements.

I claim:
1. Machine for manufacturing and packaging adhesive plasters, comprising;
    means for intermittently advancing a band of supporting material having an adhesive face and a non-adhesive face,
    a station for feeding and cutting a band of bandage material into bandage segments,
    means for coupling said bandage segments to said adhesive face of said band of supporting material,
    means for superimposing band-like protective films on said adhesive face of said band of supporting materials coupled with said bandage segments, thereby forming a composite band,
    a die-cutting station bearing means for transversely cutting said composite band in an intermediate position between said bandage segments, thereby forming individual adhesive plasters,
    means for a spaced insertion of said individual adhesive plasters between a pair of bands of packaging paper, thereby forming a final product band,
    a perforation station bearing means for providing a series of evenly spaced perforations on said band of supporting material, said perforation station being upstream from said feeding and cutting station, wherein an auxiliary band is superimposed on said non-adhesive face of said supporting material after said perforation station, said auxiliary band being closed on itself in a loop, said auxiliary band being constituted by a supporting layer of material having an adhesive face on which another band is applied, said other band having perforations through which said auxiliary band adheres to said non-adhesive face of said supporting material for a portion extending to the vicinity of said die-cutting station.

2. Machine, according to claim 1, further comprising means for providing incisions on said final product band, said means for providing incisions comprising a cutter co-operating with an abutment movable on an advancement plane of said final product band, said abutment having at least three different surfaces to provide different types of said incisions, said first surface being smooth so as to provide a total cut, said second surface having closely spaced holes so as to provide a series of closely spaced incisions, said third surface having widely spaced holes so as to provide a series of widely spaced incisions.

3. Machine, according to claim 1, wherein said station for feeding and cutting a band of bandage material into bandage segments is arranged immediately adjacent to a pair of rollers, said band of supporting material engaging around one of said rollers so that said bandage segments are retained on said adhesive face of said band of supporting material, said bandage segments being thereby regularly spaced.

4. Machine, according to claim 3, wherein said band-like protective films are superimposed on said adhesive face of said band of supporting material coupled with said bandage segments between said pair of rollers.

5. Machine, according to claim 1, wherein said die-cutting station has a reciprocatingly actuated cutting element having a substantially H-shaped blade producing a cutting line transverse to said composite band, in an intermediate position between said bandage segments, and exactly shaping the ends of said individual adhesive plasters by removing related scrap portions.

6. Machine, according to claim 1, wherein a pair of packaging rollers are arranged immediately adjacent to said die-cutting station, said individual adhesive plasters being inserted between said pair of bands of packaging paper between said pair of packaging rollers.

7. Machine, according to claim 1, wherein a band of siliconized paper is initially applied to said adhesive face of said supporting material and wherein said auxiliary band is superimposed on said non-adhesive face of said supporting material before said band of siliconized paper is removed from said adhesive face of said supporting material.

8. Machine for manufacturing and packaging adhesive plasters, comprising;
   means for intermittently advancing a band of supporting material having an adhesive face and a non-adhesive face,
   a station for feeding and cutting a band of bandage material into bandage segments,
   means for coupling said bandage segments to said adhesive face of said band of supporting material,
   means for superimposing band-like protective films on said adhesive face of said band of supporting material coupled with said bandage segments, thereby forming a composite band,
   a die-cutting station bearing means for transversely cutting said composite band in an intermediate position between said bandage segments, thereby forming individual adhesive plasters,
   means for a spaced insertion of said individual adhesive plasters between a pair of bands of packaging paper, thereby forming a final product band,
   wherein said die-cutting station has a reciprocatingly actuated cutting element having a substantially H-shaped blade producing a cutting line transverse to said composite band, in an intermediate position between said bandage segments, and exactly shaping the ends of said individual adhesive plasters by removing related scrap portions.

9. Machine, according to claim 8, further comprising a perforation station bearing means for providing a series of evenly spaced perforations on said band of supporting material, said perforation station being upstream from said feeding and cutting station.

10. Machine, according to claim 8, further comprising means for providing incisions on said final product band, said means for providing incisions comprising a cutter co-operating with an abutment movable on an advancement plane of said final product band, said abutment having at least three different surfaces to provide different types of said incisions, said first surface being smooth so as to provide a total cut, said second surface having closely spaced holes so as to provide a series of closely spaced incisions, said third surface having widely spaced holes so as to provide a series of widely spaced incisions.

11. Machine, according to claim 9, wherein an auxiliary band is superimposed on said non-adhesive face of said supporting material after said perforation station, said auxiliary band being closed on itself in a loop, said auxiliary band being constituted by a supporting layer of material having an adhesive face on which another band is applied, said other band having perforations through which said auxiliary band adheres to said non-adhesive face of said supporting material for a portion extending to the vicinity of said die-cutting station.

12. Machine, according to claim 8, wherein said station for feeding and cutting a band of bandage material into bandage segments is arranged immediately adjacent to a pair of rollers, said band of supporting material engaging around one of said rollers so that said bandage segments are retained on said adhesive face of said band of supporting material, said bandage segments being thereby regularly spaced.

13. Machine, according to claim 12, wherein said band-like protective films are superimposed on said adhesive face of said band of supporting material coupled with said bandage segments between said pair of rollers.

14. Machine, according to claim 8, wherein a pair of packaging rollers are arranged immediately adjacent to said die-cutting station, said individual adhesive plasters being inserted between said pair of bands of packaging paper between said pair of packaging rollers.

15. Machine, according to claim 8, wherein a band of siliconized paper is initially applied to said adhesive face of said supporting material and wherein said auxiliary band is superimposed on said non-adhesive face of said supporting material before said band of siliconized paper is removed from said adhesive face of said supporting material.

16. Machine for manufacturing and packaging adhesive plasters, comprising;
   means for intermittently advancing a band of supporting material having an adhesive face and a non-adhesive face,
   a station for feeding and cutting a band of bandage material into bandage segments,
   means for coupling said bandage segments to said adhesive face of said band of supporting material,
   means for superimposing band-like protective films on said adhesive face of said band of supporting material coupled with said bandage segments, thereby forming a composite band,
   a die-cutting station bearing means for transversely cutting said composite band in an intermediate position between said bandage segments, thereby forming individual adhesive plasters,
   means for a spaced insertion of said individual adhesive plasters between a pair of bands of packaging paper, thereby forming a final product band,
   means for providing incisions on said final product band, wherein said means for providing incisions comprise a cutter co-operating with an abutment movable on an advancement plane of said final product band, said abutment having at least three different surfaces to provide different types of said incisions, said first surface being smooth so as to provide a total cut, said second surface having closely spaced holes so as to provide a series of closely spaced incisions, said third surface having widely spaced holes so as to provide a series of widely spaced incisions.

17. Machine, according to claim 16, further comprising a perforation station bearing means for providing a series of evenly spaced perforations on said band of supporting material, said perforation station being upstream from said feeding and cutting station.

18. Machine, according to claim 16, wherein an auxiliary band is superimposed on said non-adhesive face of said supporting material after said perforation station, said auxiliary band being closed on itself in a loop, said auxiliary band being constituted by a supporting layer of material having an adhesive face on which another band is applied, said other band having perforations through which said auxiliary band adheres to said non-adhesive face of said supporting material for a portion extending to the vicinity of said die-cutting station.

19. Machine, according to claim 16, wherein said station for feeding and cutting a band of bandage material into bandage segments is arranged immediately adjacent to a pair of rollers, said band of supporting material engaging around one of said rollers so that said bandage segments are retained on said adhesive face of said band of supporting material, said bandage segments being thereby regularly spaced.

20. Machine, according to claim 19, wherein said band-like protective films are superimposed on said adhesive face of said band of supporting material coupled with said bandage segments between said pair of rollers.

21. Machine, according to claim 16, wherein said die-cutting station has a reciprocatingly actuated cutting element having a substantially H-shaped blade producing a cutting line transverse to said composite band, in an intermediate position between said bandage segments, and exactly shaping the ends of said individual adhesive plasters by removing related scrap portions.

22. Machine, according to claim 16, wherein a pair of packaging rollers are arranged immediately adjacent to said die-cutting station, said individual adhesive plasters being inserted between said pair of bands of packaging paper between said pair of packaging rollers.

23. Machine, according to claim 16, wherein a band of siliconized paper is initially applied to said adhesive face of said supporting material and wherein said auxiliary band is superimposed on said non-adhesive face of said supporting material before said band of siliconized paper is removed from said adhesive face of said supporting material.

24. Machine for manufacturing adhesive plasters, comprising;
   means for intermittently advancing a band of supporting material having an adhesive face and a non-adhesive face,
   a station for feeding and cutting a band of bandage material into bandage segments,
   means for coupling said bandage segments to said adhesive face of said band of supporting material,
   means for superimposing band-like protective films on said adhesive face of said band of supporting material coupled with said bandage segments, thereby forming a composite band,
   a die-cutting station bearing means for transversely cutting said composite band in an intermediate position between said bandage segments, thereby forming individual adhesive plasters,
   wherein an auxiliary band is superimposed on said non-adhesive face of said supporting material, said auxiliary band being closed on itself in a loop, said auxiliary band being constituted by a supporting layer of material having an adhesive face on which another band is applied, said other band having perforations through which said auxiliary band adheres to said non-adhesive face of said supporting material.

25. Machine, according to claim 24, wherein a band of siliconized paper is initially applied to said adhesive face of said supporting material and wherein said auxiliary band is superimposed on said non-adhesive face of said supporting material before said band of siliconized paper is removed from said adhesive face of said supporting material.

26. Machine, according to claim 24, further comprising a perforation station bearing means for providing a series of evenly spaced perforations on said band of supporting materials, said perforation station being upstream from said feeding and cutting station.

27. Machine, according to claim 24, wherein said die-cutting station has a reciprocatingly actuated cutting element having a substantially H-shaped blade producing a cutting line transverse to said composite band, in an intermediate position between said bandage segments, and exactly shaping the ends of said individual adhesive plasters by removing related scrap portions.

28. Machine, according to claim 24, further comprising means for a spaced insertion of said individual adhesive plasters between a pair of bands of packaging paper thereby forming a final product band.

29. Machine, according to claim 28, further comprising means for providing incisions on said final product band, said means for providing incisions comprising a cutter co-operating with an abutment movable on an advancement plane of said final product band, said abutment having at least three different surfaces to provide different types of said incisions, said first surface being smooth so as to provide a total cut, said second surface having closely spaced holes so as to provide a series of closely spaced incisions, said third surface having widely spaced holes so as to provide a series of widely spaced incisions.

30. Machine, according to claim 24, wherein said station for feeding and cutting a band of bandage material into bandage segments, said means for coupling said bandage segments to said adhesive face of said band of supporting material, and said means for superimposing band-like protective films on said adhesive face of said band of supporting material coupled with said bandage segments, are all structurally arranged immediately at one distinct point in said machine, said point being at a pair of rollers, said band of supporting material engaging around one of said rollers, said bank-like protective films engaging around other one of said rollers, and simultaneously at said pair of rollers, said bandage segments are cut and coupled on said adhesive face of said band of supporting material, said bandage segments being thereby regularly spaced on said band of supporting material, and said band-like protective films are superimposed on said band of supporting material coupled with said bandage segments.

31. Machine for manufacturing adhesive plasters, comprising;
   means for intermittently advancing a band of supporting material having an adhesive face and a non-adhesive face,
   a station for feeding and cutting a band of bandage material into bandage segments,
   means for coupling said bandage segments to said adhesive face of said band of supporting material,
   means for superimposing band-like protective films on said adhesive face of said band of supporting material coupled with said bandage segments, thereby forming a composite band,
   a die-cutting station bearing means for transversely cutting said composite band in an intermediate position between said bandage segments, thereby forming individual adhesive plasters,
   wherein said station for feeding and cutting a band of bandage material into bandage segments, said means for coupling said bandage segments to said adhesive face of said band of supporting material, and said means for superimposing band-like protective films on said adhesive face of said band of supporting material coupled with said bandage segments, are all structurally arranged immediately at one distinct point in said machine, said point being at a pair of rollers, said band of supporting material engaging around one of said rollers, said band-like protective films engaging around other one of said rollers, and simultaneously at said pair of rollers, said bandage segments are cut and coupled on said adhesive face of said band of supporting material, said bandage segments being thereby regularly spaced on said band of supporting material, and said band-like protective films are superimposed on said band of supporting material coupled with said bandage segments, an auxiliary band being superimposed on said non-adhesive face of said supporting material, said auxiliary band being closed on itself in a loop, said auxiliary band being constituted by a supporting layer of material having an adhesive face on which another band is applied, said other band having perforations through which said auxiliary band adheres to said non-adhesive face of said supporting material.

32. Machine, according to claim 31, wherein a band of siliconized paper is initially applied to said adhesive face of said supporting material and wherein said auxiliary band is superimposed on said non-adhesive face of said supporting material before said band of siliconized paper is removed from said adhesive face of said supporting material.

33. Machine, according to claim 31, further comprising a perforation station bearing means for providing a series of evenly spaced perforations on said band of supporting material, said perforation station being upstream from said feeding and cutting station.

34. Machine, according to claim 31, wherein said die-cutting station has a reciprocatingly actuated cutting element having a substantially H-shaped blade producing a cutting line transverse to said composite band, in an intermediate position between said bandage segments, and exactly shaping the ends of said individual adhesive plasters by removing related scrap portions.

35. Machine, according to claim 31, further comprising means for a spaced insertion of said individual adhesive plasters between a pair of bands of packaging paper thereby forming a final product band.

36. Machine, according to claim 35, further comprising means for providing incisions on said final product band, said means for providing incisions comprising a cutter co-operating with an abutment movable on an advancement plane of said final product band, said abutment having at least three different surfaces to provide different types of said incisions, said first surface being smooth so as to provide a total cut, said second surface having closely spaced holes so as to provide a series of closely spaced incisions, said third surface having widely spaced holes so as to provide a series of widely spaced incisions.

* * * * *